US006130260A

United States Patent [19]
Hall et al.

[11] Patent Number: 6,130,260
[45] Date of Patent: Oct. 10, 2000

[54] METHOD FOR CONVERTING NATURAL GAS TO LIQUID HYDROCARBONS

[75] Inventors: Kenneth R. Hall, College Station; Jerry A. Bullin; Philip T. Eubank, both of Bryan; Aydin Akgerman; Rayford G. Anthony, both of College Station, all of Tex.

[73] Assignee: The Texas A&M University Systems, College Station, Tex.

[21] Appl. No.: 09/199,502

[22] Filed: Nov. 25, 1998

[51] Int. Cl.$^7$ .............................. C07C 27/00; C07C 2/00; C07C 11/00; C07C 2/56

[52] U.S. Cl. .......................... 518/703; 585/534; 585/535; 585/540; 585/541; 585/709

[58] Field of Search ................................ 585/709, 534, 585/535, 540, 541; 518/703

[56] References Cited

U.S. PATENT DOCUMENTS

| | | |
|---|---|---|
| Re. 19,500 | 3/1935 | Youker . |
| Re. 19,794 | 12/1935 | Banck . |
| 1,023,783 | 4/1912 | Knapp . |
| 1,229,886 | 6/1917 | Cherry . |
| 1,773,611 | 8/1930 | Banck . |
| 1,800,586 | 4/1931 | Youker . |
| 1,880,307 | 10/1932 | Wulff . |
| 1,904,426 | 4/1933 | Eisenhut . |
| 1,917,627 | 7/1933 | Wulff . |
| 1,966,779 | 7/1934 | Wulff . |
| 2,028,014 | 1/1936 | Reinecke . |
| 2,037,056 | 4/1936 | Wulff . |
| 2,080,931 | 5/1937 | Rose . |
| 2,160,170 | 5/1939 | Martin et al. . |
| 2,328,864 | 9/1943 | Throckmorton . |
| 2,475,282 | 7/1949 | Hasche . |
| 2,550,089 | 4/1951 | Schlesman . |
| 2,558,861 | 7/1951 | Liggett . |
| 2,645,673 | 7/1953 | Haasche . |
| 2,675,294 | 4/1954 | Keith . |
| 2,714,126 | 7/1955 | Keith . |
| 2,751,424 | 6/1956 | Hasche . |
| 2,768,223 | 10/1956 | Williams et al. . |
| 2,986,505 | 5/1961 | Lauer et al. . |
| 3,156,733 | 11/1964 | Happel et al. . |
| 3,168,592 | 2/1965 | Cichelli et al. . |
| 3,262,757 | 7/1966 | Bodmer . |
| 3,283,028 | 11/1966 | Bergstrom et al. . |
| 3,320,146 | 5/1967 | Neely, Jr. . |
| 3,389,189 | 6/1968 | Hirayama et al. . |
| 3,409,695 | 11/1968 | Sennewald et al. . |
| 3,622,493 | 11/1971 | Crusco . |
| 3,663,394 | 5/1972 | Kawahara . |
| 3,674,668 | 7/1972 | Bjornson et al. . |
| 3,697,612 | 10/1972 | Maniero et al. . |
| 3,703,460 | 11/1972 | Shair et al . |
| 4,014,947 | 3/1977 | Krugly et al. . |
| 4,128,595 | 12/1978 | Montgomery . |
| 4,309,359 | 1/1982 | Pinto . |
| 4,336,045 | 6/1982 | Saunders et al. . |
| 4,367,363 | 1/1983 | Katz et al. . |
| 4,378,232 | 3/1983 | Peuckert et al. . |
| 4,424,401 | 1/1984 | White et al. . |
| 4,492,591 | 1/1985 | O'Reilly . |
| 4,497,970 | 2/1985 | Young . |
| 4,513,164 | 4/1985 | Olah . |
| 4,566,961 | 1/1986 | Diaz et al. . |
| 4,575,383 | 3/1986 | Lowther et al. ........................... 48/212 |
| 4,588,850 | 5/1986 | Mueller et al. . |
| 4,704,496 | 11/1987 | Paparizos et al. . |
| 4,705,906 | 11/1987 | Brophy et al. . |
| 4,705,908 | 11/1987 | Gondouin . |
| 4,757,787 | 7/1988 | Risitano et al. . |

(List continued on next page.)

OTHER PUBLICATIONS

A. Malek, et al., "Hydrogen Purification from Refinery Fuel Gas by Pressure Swing Adsorption." *AIChE Journal* vol. 44, No. 9, Sep. 1998, pp. 1985–1992.

Marshall Sittig, "Acetylene processes and Products." *Chemical Process Review* No. 22, 1968, 229 pages.

L. Bromberg, et al., "Plasma Reforming of Methane." *Energy & Fuels* Vo. 12, No. 1, 1998, pp. 11–18.

Michael j. Corke "GTL Technologies Focus on Lowering Cost." Oil & Gas Journal, Sep. 21, 1998, pp. 71–77.

Michael J. Corke, "Economics Favor GTL Projects with Condensate Coproduction." *Oil & Gas Journal* Sep. 28, 1998, pp. 96–101.

Alan H. Singleton, "Advances Make gas–to–liquids Process Competitive for Remote Locations." *Oil & Gas Journal* Aug. 4, 1997, pp. 68–72.

T. Kodama, et al., "High–Temperature Conversion of CH4 to C2–Hydrocarbons and H2 Using a Redox System of Metal Oxide." *Energy & Fuels*, vol. 11, No. 6 1997, pp. 1257–1263.

S. H. Bauer, et al., "Upgrading of Methane under Homogeneous Thermal Conditions: An Environmental and Economic Imperative." *Energy & Fuels*, vol. 11, 1997, pp. 1204–1218.

"A—Liquefied Natural Gas as a Heavy Vehicle Fuel." *Commerce Business Daily*, Jul. 17, 1997.

Lance L. Lobban, et al., "Oxidative Coupling of Methane Using an AC Electric Discharge." *American Institute of Chemical Engineers 1996 Annual Meeting, Session 37, Paper 37f.*

D. Q. kern, "Process Heat Transfer." McGraw–Hill Book Co., New Yorrk (1950).

*Primary Examiner*—Shailendra Kumar
*Assistant Examiner*—J. Parsa
*Attorney, Agent, or Firm*—Baker Botts L.L.P.

[57] ABSTRACT

A process for converting natural gas to a liquid includes heating the gas to a selected range of temperature to convert a fraction of the gas stream to reactive hydrocarbons, primarily acetylene, and reacting methane and the reactive hydrocarbons in the presence of an acidic catalyst to produce a liquid, predominantly pentane. Hydrogen resulting from the reactions is used to heat the incoming natural gas, either with a hydrogen furnace or by electrical energy generated from the hydrogen. Little or no use of methane is required to supply energy for the process.

54 Claims, 2 Drawing Sheets

U.S. PATENT DOCUMENTS

| | | |
|---|---|---|
| 4,761,515 | 8/1988 | Gondouin . |
| 4,795,536 | 1/1989 | Young et al. . |
| 4,797,185 | 1/1989 | Polak et al. . |
| 4,822,940 | 4/1989 | Leff et al. . |
| 4,906,800 | 3/1990 | Henry et al. . |
| 4,950,821 | 8/1990 | Ratnasamy et al. . |
| 4,952,743 | 8/1990 | Come . |
| 4,973,776 | 11/1990 | Allenger et al. . |
| 4,973,786 | 11/1990 | Karra . |
| 4,981,829 | 1/1991 | Shutt et al. . |
| 5,012,029 | 4/1991 | Han et al. . |
| 5,015,349 | 5/1991 | Suib et al. . |
| 5,019,355 | 5/1991 | Sackinger . |
| 5,026,944 | 6/1991 | Allenger et al. . |
| 5,053,575 | 10/1991 | Nikravech et al. . |
| 5,073,666 | 12/1991 | Zemanian et al. . |
| 5,118,893 | 6/1992 | Timmons et al. . |
| 5,131,993 | 7/1992 | Suib et al. . |
| 5,138,113 | 8/1992 | Juguin et al. . |
| 5,181,998 | 1/1993 | Murphy et al. . |
| 5,205,912 | 4/1993 | Murphy . |
| 5,205,915 | 4/1993 | Ravella et al. . |
| 5,277,773 | 1/1994 | Murphy . |
| 5,328,577 | 7/1994 | Murphy . |
| 5,472,581 | 12/1995 | Wan . |
| 5,498,278 | 3/1996 | Edlund . |
| 5,510,550 | 4/1996 | Cheung et al. . |
| 5,518,530 | 5/1996 | Sakai et al. . |
| 5,583,274 | 12/1996 | Cheung et al. . |
| 5,585,318 | 12/1996 | Johnson et al. . |
| 5,587,348 | 12/1996 | Brown et al. . |
| 5,629,102 | 5/1997 | Werth . |
| 5,675,041 | 10/1997 | Kiss et al. . |
| 5,695,618 | 12/1997 | O'Young et al. . |
| 5,714,657 | 2/1998 | de Vries . |
| 5,749,937 | 5/1998 | Detering et al. . |

METHOD FOR CONVERTING NATURAL GAS TO LIQUID HYDROCARBONS

FIELD OF THE INVENTION

This invention pertains to conversion of natural gas to liquid hydrocarbons. More particularly, methane is converted to reactive hydrocarbons and the reactive hydrocarbons are reacted with additional methane to form liquid hydrocarbons.

BACKGROUND OF THE INVENTION

Natural gas often contains about 90 mole per cent methane mixed with heavier alkanes. Alkanes of increasing carbon number are normally present in decreasing amounts. Carbon dioxide and other gases may be present.

Conversion of natural gas into hydrocarbon liquids has been a technological goal for many years. The goal has become even more important in recent years as more natural gas has been found in remote locations, where gas pipelines may not be economically justified. A significant portion of the world's reserves of natural gas occurs in such remote regions. While liquefied natural gas (LNG) and methanol projects have long attracted attention by making possible conversion of natural gas to a liquid, in recent years the advent of large scale projects based upon Fisher-Tropsch (F-T) technology have attracted more attention. A review of proposed and existing F-T projects along with a discussion of economics of the projects has recently been published (*Oil and Gas J.*, Sep. 21 and Sep. 28, 1998). In this technology, natural gas is first converted to "syngas," which is a mixture of carbon monoxide and hydrogen, and the syngas is converted to liquid paraffinic and olefinic hydrocarbons of varying chain lengths. The F-T technology was developed for using coal as a feed stock, and only two plants now operate using natural gas as feedstock—in South Africa and in Malaysia. A study showed that for a plant producing 45,000 bbls/day (BPD) of liquids in a U.S. location in 1993, investment costs would have been about $38,000 per BPD production (*Oil and Gas J.*, Sep. 28, 1998, p. 99). Improved designs are said to lower investment cost to the range of $30,000 per BPD for a 20,000 BPD facility. Such a plant would use about 180 MMSCFD of natural gas, 10 million GPD of raw water and 150 BPD of normal butane, and would produce excess steam, which could be used to produce 10 megawatts of electricity.

The conversion of methane to unsaturated hydrocarbons and hydrogen by subjecting the methane and other hydrocarbons in natural gas to high temperatures produced by electromagnetic radiation or electrical discharges has been extensively studied. U.S. Pat. No. 5,277,773 discloses a conversion process that subjects the methane plus hydrocarbons to microwave radiation so as to produce an electric discharge in an electromagnetic field. U.S. Pat. No. 5,131,993 discloses a method for cracking a hydrocarbon material in the presence of a microwave discharge plasma and a carrier gas, such as oxygen, hydrogen and nitrogen, and, generally, a catalyst. U.S. Pat. No. 3,389,189 is an example of patents relating to production of acetylene by an electric arc.

Methane pyrolysis to acetylene and hydrogen by rapid heating in a reaction zone and subsequent rapid quenching has also been extensively investigated. Subatmospheric pressures and specific ranges of velocities of hydrocarbon gases through the reaction zone are disclosed in U.S. Pat. No. 3,156,733. Heat is supplied by burning of hydrocarbons.

Although the prior art has disclosed a range of methods for forming acetylene or ethylene from natural gas, an energy-efficient process for converting natural gas to a liquid that can be transported efficiently from remote areas to market areas has not been available. What is needed is a process that does not require large capital and operating expenditures such as required by the prior art processes. Also, the process should be energy efficient, preferably energy self-sufficient, meaning that all the natural gas input should be available to convert to liquids.

SUMMARY OF THE INVENTION

A process for conversion of natural gas to a liquid for transport from remote locations is provided. In a preferred embodiment, the natural gas is heated to a temperature at which a fraction of the methane is converted to hydrogen and a reactive hydrocarbon such as acetylene, the stream is quenched to stop further reactions, and the stream is then reacted in the presence of a catalyst to form the liquid to be transported, predominantly pentane. Hydrogen may be separated after quenching and before the catalytic reactor. Heat for raising the temperature of the natural gas stream is provided by burning of hydrogen under conditions to produce a preferred range of temperature in a furnace. In another embodiment, the hydrogen produced in the process is used to generate electrical power and the electrical power is used to heat the natural gas stream. The range of temperature to which the natural gas is heated is from about 1600 to about 2500 K and preferably from about 1600 to about 1800 K. Pressure is preferably in the range from about 10 bars to about 50 bars. Little or none of the incoming natural gas is burned for fuel.

DESCRIPTION OF PREFERRED EMBODIMENTS

Figure 1:
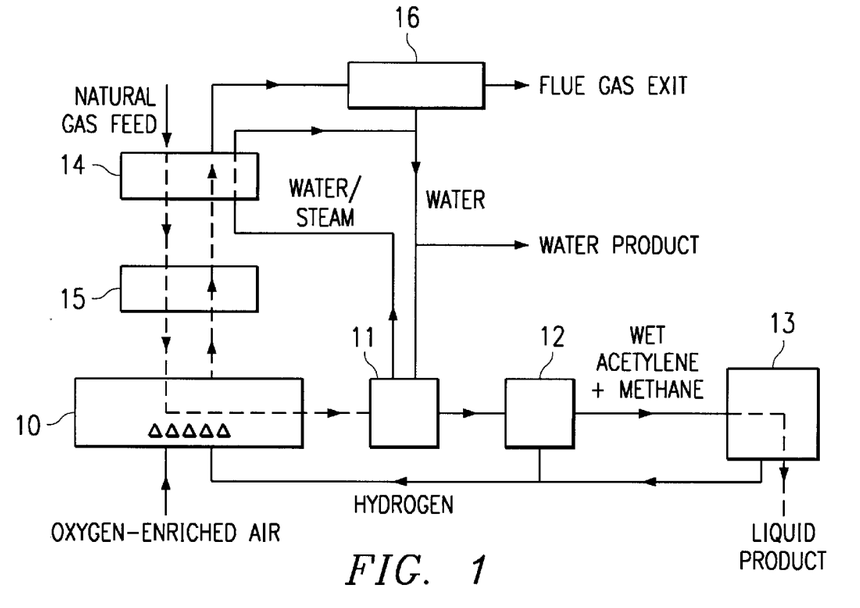
FIG. 1 shows a process diagram for one embodiment of the process of this invention in which the natural gas is heated to reaction temperature by burning of hydrogen in a furnace.

FIG. 1 shows a preferred embodiment of the steps for producing reactive gas such as acetylene from natural gas in the present invention. In this embodiment, hydrogen derived from the high temperature reactor and separated from the reactive hydrocarbon (e.g., acetylene) is directed to hydrogen combustion furnace 10, where the hydrogen is burned, preferably with oxygen-enriched air such that NOx production from the furnace is decreased. Flame temperature of hydrogen is adequate to reach a desired reaction temperature without oxygen enrichment of air, but sufficient enrichment can be easily achieved with membrane units, which are well known in the art, and this will avoid the necessity of NOx control in emissions from the furnace. Addition of water to the combustion zone of the furnace may be used to lower flame temperature to a desired range, preferably about 300 to 500 K above the preferred reaction temperature of natural gas passing through tubes in the furnace. Residence time of gas in the tubes should be long enough to convert the natural gas to acetylene and other reactive compounds and not so long as to allow significant further reactions before the quenching step, which is discussed below.

Bringing the natural gas stream, for simplicity here considered methane only, to high temperature causes one of the following reactions to occur, dependent on temperature and pressure:

or

The hydrocarbon products of the reactions are designated herein as "reactive products." The energy required to drive the reactions at a temperature of 2500 K is shown in Table 1, as calculated from data in the TRC *Thermodynamic Tables—Hydrocarbons* (available from the Thermodynamics Research Center, Texas A & M University, College Station, Tex.). Mole fractions of methane, acetylene, ethylene, hydrogen molecules and atomic hydrogen are shown for pressures of one bar, 10 bars and 50 bars. Number of moles of each material is also shown in the table. Note that energy requirements (ΔH) are slightly decreased at higher pressures and the conversion efficiency of methane to acetylene is very high. Also, the amount of atomic hydrogen produced is significantly less at pressures above 1 bar. If the moles of hydrogen produced are reacted with oxygen the enthalpy change is calculated to be 850 kJ, as shown at the bottom of the table, which is significantly more than the enthalpy required in the reaction. If the hydrogen can be utilized in a process operating at about 80% thermal efficiency, using two preheaters 14 and 15 in FIG. 1, these calculations show that the process to convert methane to acetylene can be operated at energy self-sufficient conditions at 2500 K, i.e., all the energy is derived from burning of the hydrogen that is a product of the reaction.

To stop the reactions and prevent the reverse reactions or further reactions to form carbon and other hydrocarbon compounds, rapid cooling or "quenching" is essential, in a time on-the-order-of 10–100 milliseconds. This quench may be achieved by "dumping" the reaction products into water, or, alternatively, the natural gas feed or the liquid products may be used in the quench, which may occur in vessel 11. Hydrogen may then be separated from any liquid present in separator 12 and fed to furnace 10. The reactive hydrocarbon (mostly acetylene) is then directed to low-temperature catalytic liquefaction reactor 13.

Incoming natural gas is preferably pre-heated in preheaters 14 and 15 before it is heated to the preferred reaction temperature by heat exchange with the hydrogen-combustion gas. Water is separated from the combustion gas in separator 16. Flue gas from the hydrogen furnace, water (that may be considered a product in some plant locations) and liquid hydrocarbon product are discharged from the process.

The preferred reaction temperature is in the range from about 1600 to about 2500 K. In the embodiment shown in FIG. 1, the hydrogen and acetylene or other reactive hydrocarbons are separated, with the evolved hydrogen going directly to the hydrogen furnace and the reactive hydrocarbon bottoms going to a liquefaction reactor. Alternatively, hydrogen is directed to catalytic reactor 13 without the separation step of separator 12.

The high temperature water vapor (steam) from hydrogen combustion is passed through a shell outside tubes carrying natural gas in a heat exchanger to raise the temperature of the natural gas to the selected reaction temperature and condense the steam in furnace 10. The material of construction of the furnace is not standard. Specialty materials such as tungsten or tantalum may be used. The temperature rise should occur in a short period of time. The hydrogen furnace may be of the double-radiant-section box-type as pictured in FIG. 19.5, p. 681, of D. Q. Kern, *Process Heat Transfer*, McGraw-Hill Book Co., New York (1950). The furnace may use tantalum (Ta) tubing ($170/lb.) because of its high melting point, 3269 K. Steam pressures will be low, about 6 psig. Kinetic calculations indicate a suitable time for heating the natural gas to the reaction temperature is in the range from about 1 millisecond to about 100 milliseconds. The gas is then passed out of furnace 10 to quench area 11. Water or cold natural gas or a mixture of the two may be used as quench fluid, for example. While the gas is still at a temperature above 500 K, hydrogen may be separated from the reactive hydrocarbon in gas separator 12. This separation step may be performed by any of a variety of processes, including membrane or pressure swing processes, described for example in: A. Malek and S. Farooq, "Hydrogen Purification from Refinery Fuel Gas by Pressure Swing Adsorption", *AIChE J*. 44, 1985 (1998).

Figure 2:
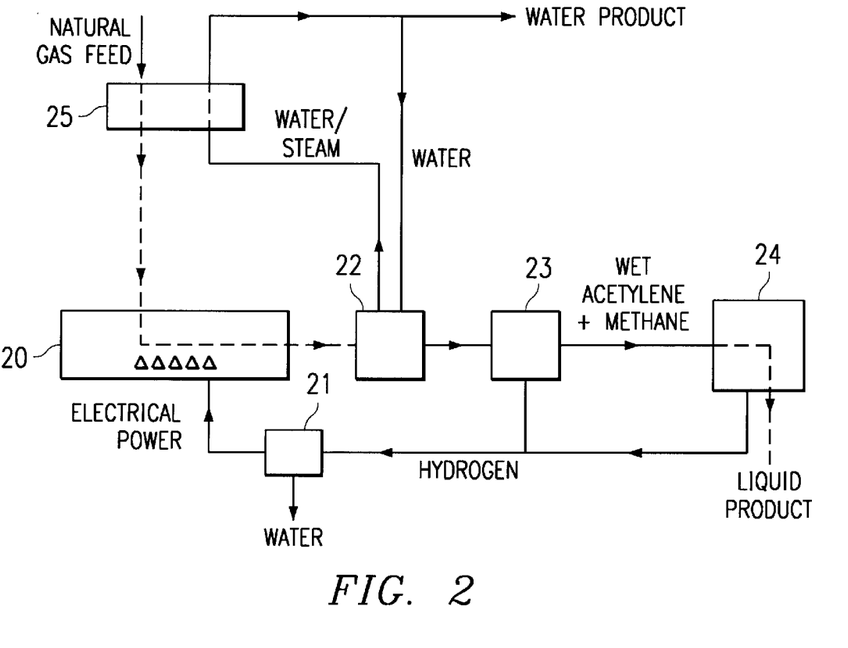
FIG. 2 shows a process diagram of another embodiment of the process of this invention in which the natural gas is heated to reaction temperature by electrical energy produced by hydrogen.

Referring to FIG. 2, a schematic diagram showing another embodiment of the method of this invention is provided. In this embodiment, natural gas is heated in high-temperature reactor 20 by means of electrical power that is produced by utilization of hydrogen in electrical power generator 21. The electrical power may be produced by fuel cells powered by hydrogen or by a combined cycle gas turbine driving electrical generators, for example. Water is also produced. Investment costs for fuel cell production of electrical power are high at present, but may be reduced by improved technology in the future. Combined cycle gas turbines are well known and at present produce electrical power at significantly lower capital costs per kW (approximately $385 per kW) than the capital costs of fuel cells (estimated at $3,000 per kW). In either case, the electrical power is used to increase temperature of the natural gas stream entering high-temperature reactor 20. The high temperature may be produced from the electrical power by an electric arc or silent discharge between electrodes, using methods well known in the art. Alternatively, the high temperature may be produced by resistance heating of carbon or other materials. In another alternative, a plasma may be formed in the natural gas stream using a "Plasmatron" such as sold by Praxair, Thermal Spray Systems, N670 Communication Drive, Appleton, Wis. 54915. Plasma temperatures are higher than the preferred temperature range for the gas reactions of this invention, so a more energy-efficient process may be achieved without bringing the natural gas to plasma temperature. The extra temperature produces extra components in the product stream that require a great deal more energy and would make the process not be as energy efficient. Quench vessel 22, separator 23, catalytic reactor 24 and preheater 25 serve functions described above relative to FIG. 1.

The reactive hydrocarbon stream coming from the hydrogen furnace or the electrically-heated reactor can be essentially one part acetylene (with small amounts of ethylene and other hydrocarbons) to three parts methane. This is the preferred feedstock for the catalytic reactor-separator 13 of FIG. 1 or the catalytic reactor-separator 24 of FIG. 2. The catalytic reactor may include recycle. The liquefaction reaction and subsequent steps can be the same for the processes depicted in FIGS. 1 and 2. The principal liquefaction reactions in the catalytic reactor are as follows:

For acetylene, and for ethylene,

This reaction must be catalyzed to suppress the reaction of acetylene to benzene and to enhance the conversion to pentane and higher compounds, which are preferred for the method of this invention.

The liquefaction reactor shown in FIGS. 1 and 2, 13 and 24 respectively, should produce predominantly pentane, but may also produce butane, hexane, heptane and some aromatic and cyclic compounds. The vapor pressure of pentane is about 1 bar at 40° C. Thus, it can be transported via truck or ship. Heavier hydrocarbons such as crude oil may be added to the produced liquid to reduce vapor pressure of a liquid to be transported.

The reaction to produce pentane is thermodynamically favorable. The equilibrium thermodynamics for the reactions of acetylene and ethylene with methane are more favorable at low to moderate temperatures (300–1000 K). It is well known in the chemical industry that alkanes of ethane and higher can be converted to higher molecular weight hydrocarbons using the zeolite catalyst H-ZSM-5. The acidity of H-ZSM-5 can be varied by altering the silica to alumina ratio in the catalyst (typical ratios range from 30 to 30,000) to make possible alkylation of acetylene with methane, thus forming higher molecular weight hydrocarbons, predominantly pentane. Other alkylation catalysts are known in the chemical industry. In the present invention, the reaction of acetylene and ethylene to benzene is suppressed and the reaction of these reactive hydrocarbons with methane is enhanced. Steam may be introduced into the reactor to achieve the desired conversion results. The preferred reactor conditions are temperature in the range from about 300 to about 800 k and pressure in the range from about 2 to about 30 bar.

It should be understood that a cooling step and a separation step may be considered a part of the catalytic reactor of FIGS. 1 and 2 (13 and 24, respectively). Cooling of the stream after the reaction may be necessary, depending upon the method of final separation and the optimum conditions for that separation. If the separation is simply a gas-liquid or flash separation, cooling may be necessary. Distillation, adsorption or absorption separation processes, including pressure-swing adsorption and membrane separation, may be used for the final separation. Any known hydrocarbon liquid-gas separation processes may be used for the final separation step, which is considered a part of the catalytic reactor. Liquid hydrocarbon then goes to storage or transport facilities and hydrogen is transported to the furnace shown is FIG. 1 or the electrical generation method discussed above in connection with FIG. 2.

Figure 3:
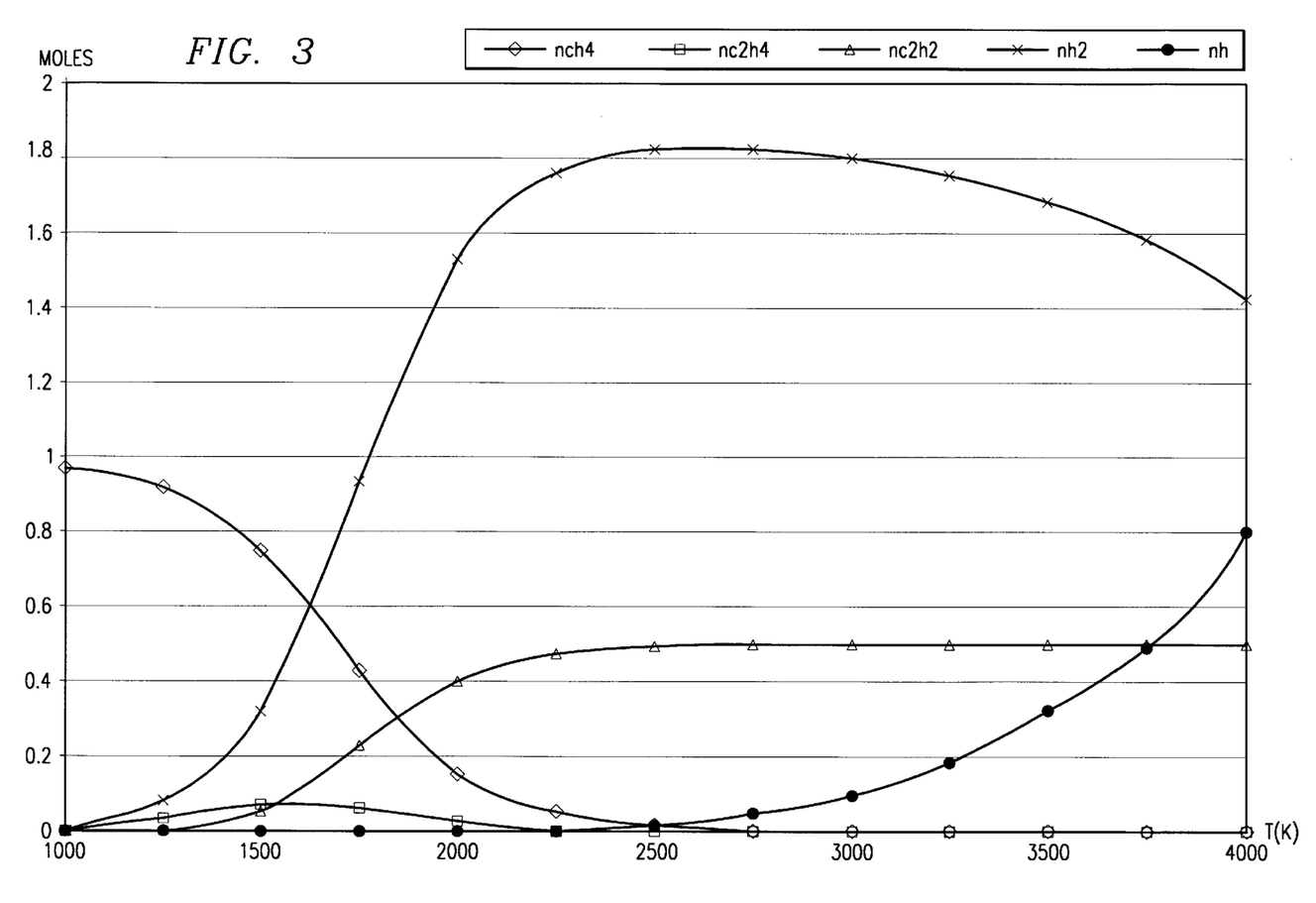
FIG. 3 shows a graph of equilibrium values of moles of species formed from one mole of methane as a function of temperature of reaction at a pressure of 10 bars.

FIG. 3 shows a plot of number of moles of each species versus temperature for a pressure of 10 bars, starting with one mole of methane. Note that at a temperature in the range of 2500 K very little methane is present and that at about 1700 K the ratio of acetylene and methane is approximately correct for the liquefaction reactor (3 moles methane per mole acetylene). A near maximum amount of molecular hydrogen is present at 2500 K; this amount drops off at higher temperatures because of the formation of atomic hydrogen, as indicated by the curve near the bottom of the figure. The amount of ethylene present increases and is a maximum at about 1500 K. Kinetic calculations indicate that optimum ethylene production would require a reaction time of only a few microseconds, which is a practical impossibility. Ethylene concentration would then decrease as it is converted to acetylene. Kinetic calculations also indicate that acetylene concentration builds to its equilibrium value in times of a few milliseconds up to about 100 milliseconds.

Although 2500 K appears to be near an optimum temperature in FIG. 4 for total conversion to acetylene, it is preferable with the hydrogen furnace reactor to use a temperature nearer to 1700 K, preferably in the range from about 1600 K to about 1800 K. While the entire stream must be treated at temperature in this embodiment, the heat exchange and energy requirement loads are greatly reduced as compared with converting the maximum amount of methane to acetylene.

Tables 1, 2 and 3 show the calculations of the mole fractions and number of moles of each reactant when two moles of methane are at equilibrium at temperatures of 2500 K, 2000 K and 3000 K, respectively. These calculations are shown at pressures of 1 bar, 10 bars and 50 bars. Also shown are the change in enthalpy during the reaction of two moles and the change in enthalpy ($\Delta H$) per mole of methane. These calculations were performed using the method described in chemical engineering thermodynamics textbooks, such as *Introduction to Chemical Engineering Thermodynamics* by Smith, Van Ness and Abbott (McGraw-Hill). A notation at the bottom of Table 1 indicates that the moles of hydrogen produced may then be burned with oxygen to produce 850 kJ at 100% thermal efficiency. Thus, little or no consumption of natural gas for fuel will be necessary.

Referring to the tables, it can be seen that higher temperatures are required for converting substantially all the methane to reactive molecules at higher pressures. For example, in Table 2 it is shown that at 2000 K, 16 per cent of the mole of methane is still present at 50 bars, whereas conversion of methane to reactive hydrocarbons is almost complete at 1 bar. At 1 bar, however, much larger heat exchange vessels would be required, causing increased capital costs, so 10 bars is a more preferred pressure. Referring to Table 1, at 10 bars a very high mole fraction of methane is converted at 2500 K. At 3000 K (Table 3), conversion of methane is very high even at a pressure of 50 bars. Therefore, reactor pressure in the range of 10 bars and higher temperatures are preferred. Energy requirements ($\Delta H$) for the reaction decrease at higher pressures.

As discussed above in reference to prior art, using present Fischer-Tropsch (F-T) technology to convert natural gas to liquid, investment costs for a plant to produce 45,000 bbls/day (BPD) of liquids in a U.S. location in 1993 would have been about $38,000 per BPD production (*Oil and Gas J.*, Sep. 28, 1998, p. 99). Improved designs are said to lower investment cost to the range of $30,000 per BPD for a 20,000 BPD facility. Such a plant would use about 180 MMSCFD of natural gas, 10 million GPD of raw water and 150 BPD of normal butane, and would produce excess steam, which could be used to produce 10 megawatts of electricity. In this process, all the natural gas is burned, with about 50% going into syngas and 50% going to supply energy for the process.

In the preferred embodiment of the present invention wherein a hydrogen furnace is used to produce the reactive hydrocarbons under preferred conditions and methane is then reacted with the reactive hydrocarbons to produce 20,000 BPD of liquid, the process would require only 116 MMSCFD of natural gas, no butane, and it would produce 45,500 gal/day (GPD) of water. The capital cost of this plant is estimated to range between $87 million and $231 million, using the furnace and other vessels as described above. For the F-T process producing the same amount of liquid, the capital cost is about $600 million (at $30,000 per BPD) Thus, capital costs for the process of the present invention are estimated to be in the range from about $4,350 per BPD to $11,500 per BPD for a 20,000 BPD plant, as compared with $30,000 per BPD for a F-T plant. The other option for producing liquid hydrocarbon, using LNG, is estimated to cost more than the F-T process. The large difference in capital costs and the requirement for little or no burning of natural gas for energy in the process of this invention are surprising.

EXAMPLE 1

The method of this invention is used in a large plant for converting natural gas to liquid. A 2-gigawatt electrical power plant is located remotely from a large natural gas field and costs of a pipeline connecting the two prevent development of the natural gas field. Equipment for the process shown in FIG. 1 is provided near the location of the gas field. The power plant requires about 5 billion BTU per day of fuel. This amount of fuel requires a gas-to-liquid plant treating about 6,000 standard cubic feet per second of natural gas, or 520 million standard cubic feet per day. The plant produces about 3.6 million GPD of liquid hydrocarbons that can be sent by truck, train or ship to the power plant, and about 2.25 million GPD of water, enough to supply a town with a population of 30,000, or, alternatively, to irrigate about 2,500 acres of desert for crop production. The plant, requiring only a furnace for burning the hydrogen and widely available equipment for the quenching, liquefaction and separation steps, requires far less capital investment than a plant based upon the F-T process. In addition, little or no energy costs are associated with operation of the plant because the hydrogen produced in the process provides sufficient energy in the furnace.

EXAMPLE 2

A remote natural gas well produces natural gas at a rate of 10 million standard cubic feet per day. The gas from this well is liquefied for truck transport to a market. The process of FIG. 1 is applied using trailer-mounted vessels to produce 1,725 BPD of liquid hydrocarbons. The capital cost of the equipment is about $20 million, or about $11,600 per BPD capacity. The plant is moved to other wells when production from the initial well declines to an uneconomic rate.

Although the present invention has been described with reference to specific details, it is not intended that such details should be regarded as limitations upon the scope of the invention, except as and to the extent that they are included in the accompanying claims.

TABLE 1

Energy Required by the High Temperature Reactor at 2,500 K.
$2CH4 = iC2H2 + jC2H4 + kH2 + lH$

| Compound | 1 bar | | 10 bar | | 50 bar | |
|---|---|---|---|---|---|---|
| | x | n | x | n | x | n |
| CH4 (g) | 0.00046 | 0.00157 | 0.00457 | 0.01567 | 0.02187 | 0.07176 |
| C2H2 (g) | 0.14601 | 0.49890 | 0.14261 | 0.48902 | 0.13711 | 0.44991 |
| C2H4 (g) | 0.00009 | 0.00032 | 0.00092 | 0.00314 | 0.00433 | 0.01421 |
| H2 (g) | 0.83045 | 1.82496 | 0.84452 | 1.81185 | 0.83340 | 1.68762 |
| H (g) | 0.02299 | 0.05053 | 0.00739 | 0.01586 | 0.00329 | 0.00666 |
| ΔH (kJ) | 648 | | 637 | | 622 | |
| ΔH (kJ/mol Cl) | 324 | | 318 | | 311 | |

Note:
we have 850 kJ available from the hydrogen produced in the process

TABLE 2

Energy Required by the High Temperature Reactor at 2,000 K.
$2CH4 = iC2H2 + jC2H4 + kH2 + lH$

| Compound | 1 bar | | 10 bar | | 50 bar | |
|---|---|---|---|---|---|---|
| | x | n | x | n | x | n |
| CH4 (g) | 0.00500 | 0.01721 | 0.04506 | 0.13980 | 0.16146 | 0.38846 |
| C2H2 (g) | 0.14176 | 0.48847 | 0.13111 | 0.40675 | 0.10165 | 0.24458 |
| C2H4 (g) | 0.00085 | 0.00293 | 0.00753 | 0.02335 | 0.02543 | 0.06119 |
| H2 (g) | 0.85083 | 1.81628 | 0.81581 | 1.54213 | 0.71125 | 0.99890 |
| H (g) | 0.00157 | 0.00335 | 0.00049 | 0.00920 | 0.00020 | 0.00029 |
| ΔH (kJ) | 559 | | 532 | | 473 | |
| ΔH (kJ/mol Cl) | 279 | | 266 | | 237 | |

Note:
we have 850 kJ available from the hydrogen produced in the process

TABLE 3

Energy Required by the High Temperature Reactor at 3,000 K.
$2CH4 = iC2H2 + jC2H4 + kH2 + lH$

| Compound | 1 bar | | 10 bar | | 50 bar | |
|---|---|---|---|---|---|---|
| | x | n | x | n | x | n |
| CH4 (g) | 0.00001 | 0.00027 | 0.00092 | 0.00308 | 0.00461 | 0.01562 |
| C2H2 (g) | 0.16041 | 0.49980 | 0.14874 | 0.49775 | 0.14428 | 0.48866 |
| C2H4 (g) | 0.00009 | 0.00007 | 0.00021 | 0.00072 | 0.00104 | 0.00353 |
| H2 (g) | 0.71641 | 1.69345 | 0.80699 | 1.79569 | 0.83026 | 1.79600 |
| H (g) | 0.12307 | 0.29091 | 0.04314 | 0.00960 | 0.01980 | 0.04284 |
| ΔH (kJ) | 801 | | 736 | | 741 | |
| ΔH (kJ/mol Cl) | 401 | | 368 | | 370 | |

Note:
we have 850 kJ available from the hydrogen produced in the process

What we claim is:

1. A method for converting natural gas to a hydrocarbon liquid and water, comprising the steps of:
    a) providing a stream of natural gas at a selected pressure;
    b) conveying the natural gas through a furnace wherein hydrogen is burned while controlling temperature of the flame and wherein the natural gas is heated to a selected range of temperature to cause a chemical reaction forming reactive products and hydrogen;
    c) quenching the reactive products and hydrogen;
    d) conveying the reactive products and hydrogen to a catalytic liquefaction reactor and providing natural gas and a catalyst in the reactor such that the reactive products and natural gas react to produce hydrogen and the hydrocarbon liquid;
    e) conveying hydrogen from the catalytic liquefaction reactor to the hydrogen furnace for burning so as to heat the natural gas and produce water; and
    f) conveying the liquid hydrocarbon and the water to storage or transport.

2. The method of claim 1 wherein the selected pressure of the natural gas stream is between about 1 bar and about 50 bars.

3. The method of claim 1 wherein the selected pressure of the natural gas stream is between about 7 bars and about 12 bars.

4. The method of claim 1 wherein in step b) the natural gas is heated to a temperature in the range from about 1600 K to about 2500 K.

5. The method of claim 1 wherein in step b) the natural gas is heated to a temperature in the range from about 1600 K to about 1800 K.

6. The method of claim 1 wherein the catalyst in the catalytic liquefaction reactor is an acid catalyst.

7. The method of claim 6 wherein the acid catalyst is a zeolite-based catalyst and the acidity of the catalyst is increased by introduction of additional silica into the catalyst.

8. The method of claim 1 further comprising the step of introducing steam into the catalytic liquefaction reactor.

9. The method of claim 1 wherein the temperature in the catalytic liquefaction reactor is in the range from about 300 K to about 1000 K.

10. The method of claim 1 wherein the pressure in the catalytic liquefaction reactor is in the range from about 2 bars to about 30 bars.

11. The method of claim 1 wherein the hydrogen is burned using oxygen-enriched air.

12. The method of claim 1 wherein in step b) the temperature of the flame is controlled by supplying water while burning the hydrogen.

13. A method for converting natural gas to a hydrocarbon liquid and water, comprising the steps of:
   a) providing a stream of natural gas at a selected pressure;
   b) conveying the natural gas through a furnace wherein hydrogen is burned while controlling the temperature of the flame and wherein the natural gas is heated to a selected range of temperature to cause a chemical reaction forming reactive products and hydrogen;
   c) quenching the reactive products and hydrogen;
   d) conveying the reactive products and hydrogen to a separator and separating the reactive products and hydrogen to form a first hydrogen stream and a reactive product stream and conveying the first hydrogen stream to the hydrogen furnace for burning;
   e) conveying the reactive product stream to a catalytic liquefaction reactor and providing natural gas and a catalyst in the reactor such that the reactive products and natural gas react to produce hydrogen and the hydrocarbon liquid;
   f) conveying a second hydrogen stream from the catalytic liquefaction reactor to the hydrogen furnace for burning so as to heat the natural gas and produce water; and
   g) conveying the liquid hydrocarbon and the water to storage or transport.

14. The method of claim 13 wherein the selected pressure of the natural gas stream is between about 1 bar and about 50 bars.

15. The method of claim 13 wherein the selected pressure of the natural gas stream is between about 7 bars and about 12 bars.

16. The method of claim 13 wherein in step b) the natural gas is heated to a temperature in the range from about 1600 K to about 2500 K.

17. The method of claim 13 wherein in step b) the natural gas is heated to a temperature in the range from about 1600 K to about 1800 K.

18. The method of claim 13 wherein the catalyst in the catalytic liquefaction reactor is an acid catalyst.

19. The method of claim 18 wherein the acid catalyst is a zeolite-based catalyst and acidity of the catalyst is increased by introduction of additional silica into the catalyst.

20. The method of claim 13 further comprising the step of introducing steam into the catalytic liquefaction reactor.

21. The method of claim 13 wherein the temperature in the catalytic liquefaction reactor is in the range from about 300 K to about 1000 K.

22. The method of claim 13 wherein the pressure in the catalytic liquefaction reactor is in the range from about 2 bars to about 30 bars.

23. The method of claim 13 wherein the hydrogen is burned using oxygen-enriched air.

24. The method of claim 13 wherein in step b) the temperature of the flame is controlled by supplying water while burning the hydrogen.

25. A method for converting natural gas to a hydrocarbon liquid and water, comprising the steps of:
   a) providing a stream of natural gas at a selected pressure;
   b) conveying the natural gas to a reactor having means for heating the natural gas using electrical power, wherein the natural gas is heated to a selected range of temperature to cause a chemical reaction forming reactive products and hydrogen;
   c) quenching the reactive products and hydrogen;
   d) conveying the reactive products and hydrogen to a catalytic liquefaction reactor and providing natural gas and a catalyst in the liquefaction reactor such that the reactive products and natural gas react to produce hydrogen and the hydrocarbon liquid;
   e) conveying hydrogen from the catalytic liquefaction reactor to a means for generating electrical power and producing water;
   f) conveying the electrical power from the means for generating electrical power to the reactor having means for heating using electrical power; and
   g) conveying the liquid hydrocarbon and the water to storage or transport.

26. The method of claim 25 wherein in step b) the means for heating the natural gas using electrical power is an electric arc.

27. The method of claim 25 wherein in step b) the means for heating the natural gas is resistance heating.

28. The method of claim 25 wherein in step b) the means for heating the natural gas is a plasma.

29. The method of claim 25 wherein in step e) the means for generating electrical power is a fuel cell.

30. The method of claim 25 wherein in step e) the means for generating electrical power is a combined cycle gas turbine driving electrical generators.

31. The method of claim 25 wherein the selected pressure of the natural gas stream is between about 1 bar and about 50 bars.

32. The method of claim 25 wherein the selected pressure of the natural gas stream is between about 7 bars and about 12 bars.

33. The method of claim 25 wherein in step b) the natural gas is heated to a temperature in the range from about 1600 K to about 2500 K.

34. The method of claim 25 wherein in step b) the natural gas is heated to a temperature in the range from about 1600 K to about 1800 K.

35. The method of claim 25 wherein the catalyst in the catalytic liquefaction reactor is an acid catalyst.

36. The method of claim 35 wherein the acid catalyst is a zeolite-based catalyst and the acidity of the catalyst is increased by introduction of additional silica into the catalyst.

37. The method of claim 25 further comprising the step of introducing steam into the catalytic liquefaction reactor.

38. The method of claim 25 wherein the temperature in the catalytic liquefaction reactor is in the range from about 300 K to about 1000 K.

39. The method of claim 25 wherein the pressure in the catalytic liquefaction reactor is in the range from about 2 bars to about 30 bars.

40. A method for converting natural gas to a hydrocarbon liquid and water, comprising the steps of:

a) providing a stream of natural gas at a selected pressure;

b) conveying the natural gas to a reactor having means for heating the natural gas using electrical power, wherein the natural gas is heated to a selected range of temperature to cause a chemical reaction forming reactive products and hydrogen;

c) quenching the reactive products and hydrogen;

d) conveying the reactive products and hydrogen to a separator and separating the reactive products and hydrogen to form a first hydrogen stream and a reactive product stream and conveying the first hydrogen stream to a means for generating electrical power and producing water;

e) conveying the reactive products to a catalytic liquefaction reactor and providing natural gas and a catalyst in the liquefaction reactor such that the reactive products and natural gas react to produce hydrogen and the hydrocarbon liquid;

f) conveying a second hydrogen stream from the catalytic liquefaction reactor to the means for generating electrical power and producing water;

g) conveying the electrical power from the means for generating electrical power to the reactor having means for heating using electrical power; and h) conveying the liquid hydrocarbon and the water to storage or transport.

41. The method of claim 40 wherein in step b) the means for heating the natural gas using electrical power is an electric arc.

42. The method of claim 40 wherein in step b) the means for heating the natural gas using electrical power is resistance heating.

43. The method of claim 40 wherein in step b) the means for heating the natural gas is a plasma.

44. The method of claim 40 wherein in step e) the means for generating electrical power is a fuel cell.

45. The method of claim 40 wherein in step e) the means for generating electrical power is a combined cycle gas turbine driving electrical generators.

46. The method of claim 40 wherein the selected pressure of the natural gas stream is between about 1 bar and about 50 bars.

47. The method of claim 40 wherein the selected pressure of the natural gas stream is between about 7 bars and about 12 bars.

48. The method of claim 40 wherein in step b) the natural gas is heated to a temperature in the range from about 1600 K to about 2500 K.

49. The method of claim 40 wherein in step b) the natural gas is heated to a temperature in the range from about 1600 K to about 1800 K.

50. The method of claim 40 wherein the catalyst in the catalytic liquefaction reactor is an acid catalyst.

51. The method of claim 50 wherein the acid catalyst is a zeolite-based catalyst and the acidity of the catalyst is increased by introduction of additional silica into the catalyst.

52. The method of claim 40 further comprising the step of introducing steam into the catalytic liquefaction reactor.

53. The method of claim 40 wherein the temperature in the catalytic liquefaction reactor is in the range from about 300 K to about 1000 K.

54. The method of claim 40 wherein the pressure in the catalytic liquefaction reactor is in the range from about 2 bars to about 30 bars.

* * * * *

UNITED STATES PATENT AND TRADEMARK OFFICE
CERTIFICATE OF CORRECTION

PATENT NO. : 6,130,260
DATED : October 10, 2000
INVENTOR(S) : Kenneth R. Hall, et al It is certified that error appears in the above-identified patent and that said Letters Patent is hereby corrected as shown below:

Title page,
Item [56] References Cited, Other Publications, insert -- Oliver Michael Gondouin, "Natural Gas Conversion Process." *Department of Energy Tech Brief,* December 1993, 8 pp --.

Column 4,
Line 3, after "the", delete "double-radiant-section box-type", and insert -- *double-radiant-section box-type* --.

Signed and Sealed this

Twenty-third Day of October, 2001

Attest:

NICHOLAS P. GODICI
Attesting Officer
Acting Director of the United States Patent and Trademark Office